United States Patent [19]

Gravlee, Jr.

[11] Patent Number: 5,733,266
[45] Date of Patent: Mar. 31, 1998

[54] HYPODERMIC NEEDLE

[76] Inventor: Joseph F. Gravlee, Jr., 557 N. Mobile St., Fairhope, Ala. 36533-1028

[21] Appl. No.: 686,949

[22] Filed: Jul. 26, 1996

[51] Int. Cl.$^6$ ................................................. A61M 5/32
[52] U.S. Cl. ............................................. 604/272; 606/223
[58] Field of Search ............................... 604/272, 264, 604/273, 274, 222, 223, 224

[56] References Cited

U.S. PATENT DOCUMENTS

| | | |
|---|---|---|
| 2,555,493 | 6/1951 | Kirschbaum . |
| 3,330,268 | 7/1967 | Goldsmith . |
| 3,589,363 | 6/1971 | Banko et al. . |
| 3,693,613 | 9/1972 | Kelman . |
| 3,805,787 | 4/1974 | Banko . |
| 3,930,505 | 1/1976 | Wallach . |
| 4,027,668 | 6/1977 | Dunn . |
| 4,490,139 | 12/1984 | Huizenga et al. ............... 604/264 X |
| 4,689,040 | 8/1987 | Thompson . |
| 4,702,260 | 10/1987 | Wang . |
| 4,959,049 | 9/1990 | Smirmaul . |
| 5,162,044 | 11/1992 | Gahn et al. . |
| 5,213,569 | 5/1993 | Davis . |
| 5,254,082 | 10/1993 | Takase . |
| 5,286,256 | 2/1994 | Mackool . |
| 5,292,310 | 3/1994 | Yoon . |
| 5,536,259 | 7/1996 | Uttenberg ........................ 604/272 |
| 5,575,780 | 11/1996 | Saito ................................ 604/272 |

*Primary Examiner*—John D. Yasko
*Attorney, Agent, or Firm*—Burns, Doane, Swecker & Mathis, L.L.P.

[57] ABSTRACT

A hypodermic needle according to the present invention includes a hollow shaft having a substantially cylindrical inner surface and a substantially cylindrical outer surface. The needle includes a beveled surface extending between and connecting the inner surface and the outer surface of the needle tip. A cutting edge of the needle is formed between the beveled surface and the internal surface of the needle. The hypodermic needle avoids trauma, tearing, and other unnecessary tissue damage during penetration of tissue and during threading of the probe through blood vessels, tunnel incisions or cavities. An alternative embodiment of the hypodermic needle has a cutting edge which includes a rounded or blunted section at a trailing portion of the cutting edge.

18 Claims, 3 Drawing Sheets

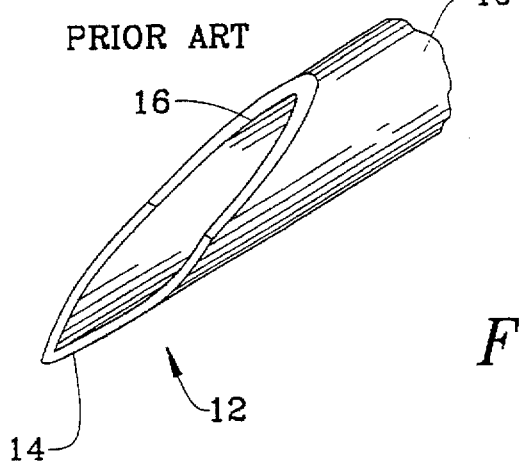
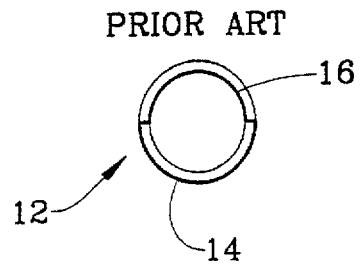
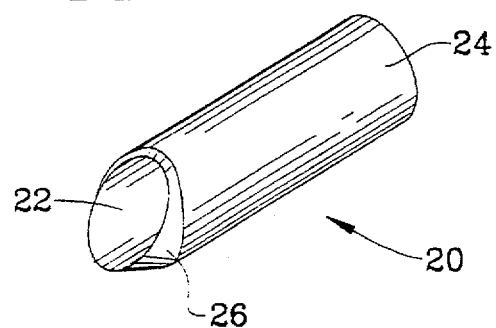
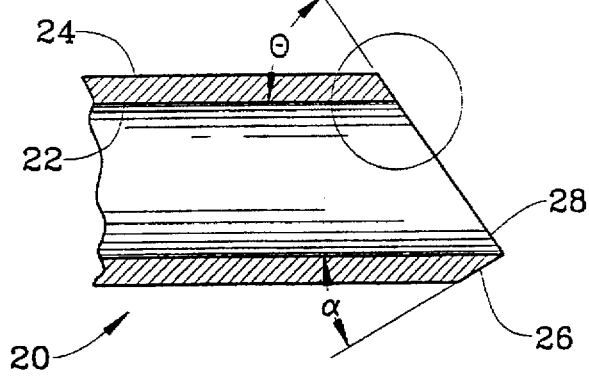
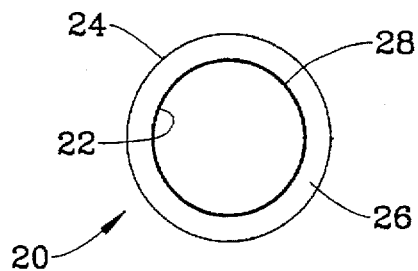
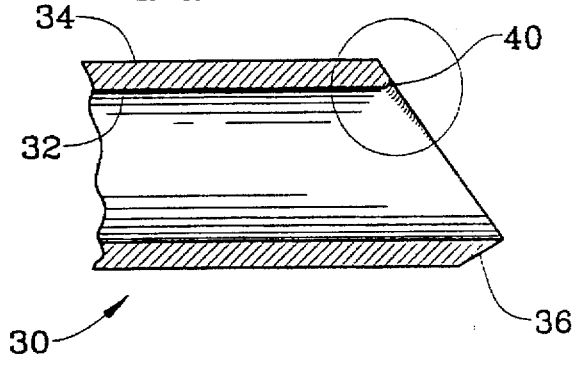
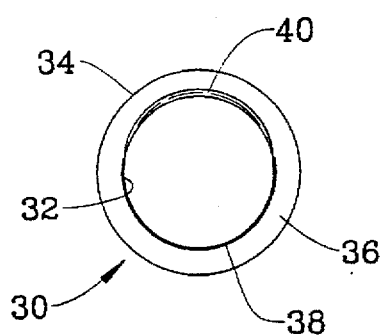

FIG. 8
FIG. 9
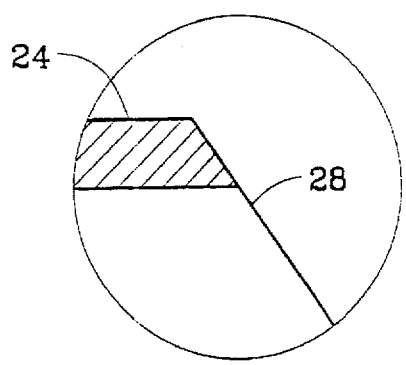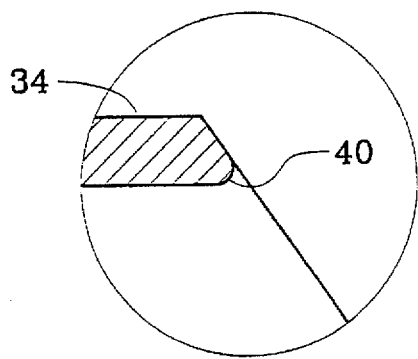
FIG. 10
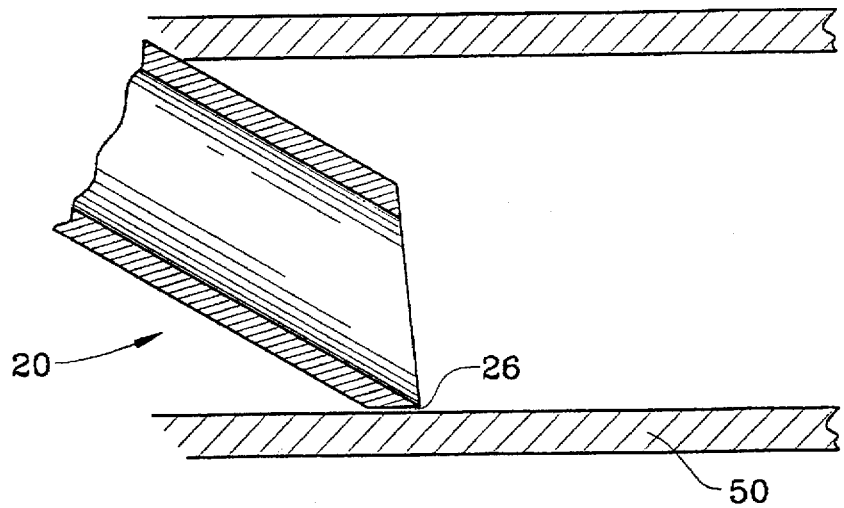
FIG. 11
PRIOR ART
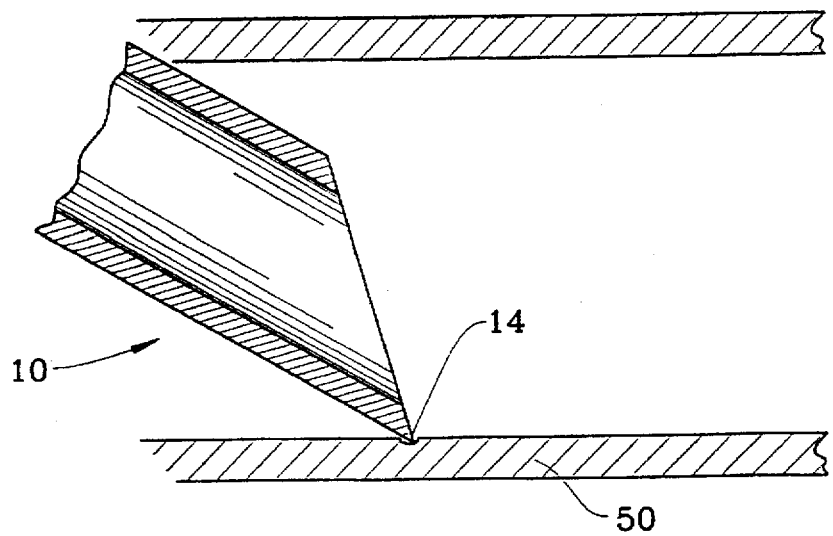

5,733,266

HYPODERMIC NEEDLE

FIELD OF THE INVENTION

The present invention relates to a hypodermic needle having an angled needle tip with an improved cutting edge which causes less trauma to tissue during insertion than conventional hypodermic needles.

BACKGROUND OF THE INVENTION

Hypodermic needles are used in the medical field primarily for injecting medications beneath the skin and for drawing blood from veins. A conventional hypodermic needle is illustrated in FIG. 1 and includes a hollow needle shaft 10 and an angled cutting tip 12. The cutting tip 12 of the conventional hypodermic needle includes a leading cutting edge 14 which is formed along a portion of the exterior diameter of the needle shaft 10 and a trailing cutting edge 16 which is formed along a portion of the interior diameter of the needle shaft.

As the cutting tip 12 of the conventional hypodermic needle is inserted into the tissue of a patient, the cutting edge changes from the exterior cutting edge 14 to the interior cutting edge 16. This change of the cutting edge causes various disadvantages including trauma and tearing of the tissues being pierced and difficulty in penetrating the tissue. This trauma and tearing of the tissue due to the nature of the cutting edge results in pain to the patient and tissue damage which can take a relatively long period of time to heal. In addition, the location of the leading cutting edge 14 at the exterior diameter of the needle shaft 10 creates a tendency of the needle to deviate from an intended course and damage of surrounding tissue. The location of the leading cutting edge 14 also makes it difficult to thread the needle through a vessel, tunnel incision, or cavity without causing trauma to the tissue due to the leading cutting edge becoming caught on the walls of the vessel, tunnel incision, or cavity.

A further drawback associated with hypodermic needles configured in the manner shown in FIG. 1 is that they tend to produce a "plug" of body tissue when they penetrate the skin or a "plug" of tissue when they pass through the wall of a blood vessel. If the hypodermic needle is used to administer medicine, drugs, or the like, the "plug" of tissue in the needle is pushed out of the needle during administration of the medicine, drugs, or the like, and is delivered to the place of administration. The plug of tissue tends to be even larger than the internal diameter of the needle because the flat leading edge 14 of the prior art needle tends to funnel or jam tissue into the bore of the needle which is then amputated by the sharp trailing edge 16. It is believed that this "plug" of tissue could present problems insofar as causing either a sterile or an infectious abscess. A sterile abscess would be caused by the body's immune reaction to the non-viable injected tissue. Sterile abscesses are commonly attributed to the medicine injected rather than recognized or admittedly secondary to reverse biopsy or the iatrogenic injection of tissue plugs. The etiology of an infectious abscess would be the body's immune reaction to germs on the skin incorporated within the plug of tissue injected within the body. This may occur in spite of pre-procedure preparing with alcohol or antibacterial soaps.

An additional drawback of the conventional hypodermic needle due to the nature of the pointed needle tip is illustrated by FIG. 11. As shown in FIG. 11, the leading cutting edge 14 of the conventional hypodermic needle 10 is likely to puncture or otherwise damage an opposite side wall of a blood vessel 50 on the side opposite the point of entry of the needle if the needle is allowed to penetrate too deeply into the blood vessel. Double perforation of blood vessels by inserting the prior art needle too far is probably the most common reason why phebotomists abandon a site ("blown vein") and try again at another site.

SUMMARY OF THE INVENTION

The hypodermic needle according to the preferred embodiments of the present invention addresses the disadvantages of conventional hypodermic needles by providing a needle which avoids trauma, tearing, and other unnecessary tissue damage during penetration of tissue and during threading of the probe through blood vessels, tunnel incisions, or cavities. The present invention also prevents deviation of the hypodermic needle from its intended path (or a plough effect) during insertion which occurs with the conventional hypodermic needles.

In accordance with one aspect of the present invention, a hypodermic needle includes an internal substantially cylindrical surface, an external substantially cylindrical surface, a distal end formed at an angle with respect to an axis of the needle, a beveled surface extending around a portion of the distal end and forming an acute angle with the internal surface, and a leading cutting edge formed by an intersection of the beveled surface and the internal surface.

In accordance with another aspect of the present invention, a hypodermic needle includes a hollow needle shaft having a longitudinal axis and an internal diameter, a needle distal end formed at an acute angle with respect to the longitudinal axis of the needle shaft, and a leading cutting edge formed at the internal diameter of the needle shaft and extending along at least a portion of an internal circumference of the needle.

BRIEF DESCRIPTION OF THE DRAWING FIGURES

The invention will be described in greater detail with reference to the accompanying drawings in which like elements bear like reference numerals, and wherein:

FIG. 1 is a perspective view of a prior art hypodermic needle;

FIG. 2 is an end view of the prior art hypodermic needle of FIG. 1;

FIG. 3 is a perspective view of a hypodermic needle according to the present invention;

FIG. 4 is a cross-sectional side view of the hypodermic needle of FIG. 3;

FIG. 5 is an end view of the hypodermic needle of FIG. 3;

FIG. 6 is a cross-sectional side view of an alternative embodiment of the hypodermic needle according to the present invention;

FIG. 7 is an end view of the hypodermic needle of FIG. 6;

FIG. 8 is an enlarged view of the circled portion of FIG. 4;

FIG. 9 is an enlarged view of the circled portion of FIG. 6;

FIG. 10 is a side view of the hypodermic needle of FIG. 4 inserted in a vein;

FIG. 11 is a side view of the prior art hypodermic needle inserted in a vein;

DETAILED DESCRIPTION OF THE PREFERRED EMBODIMENT

Figure 12:
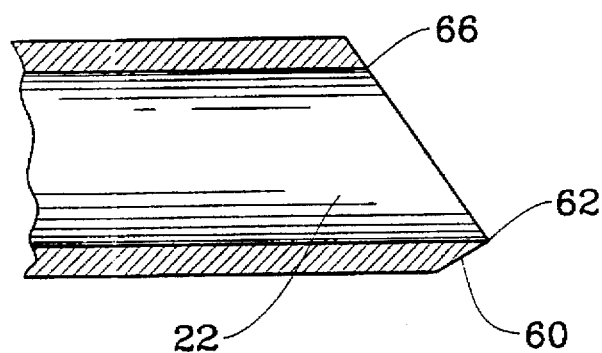
FIG. 12 is a cross-sectional view of an alternative embodiment of the hypodermic needle according to the present invention.

The tip of a hypodermic needle 20 according to a first embodiment of the present invention is shown in FIGS. 3–5. The hypodermic needle 20 includes a hollow shaft having a substantially cylindrical inner surface 22 and a substantially cylindrical outer surface 24. The needle includes a beveled surface 26 extending between and connecting the inner surface 22 and the outer surface 24 of the needle tip. A cutting edge of the needle is formed between the beveled surface 26 and the internal surface 22 of the needle.

The needle tip of the present invention may be formed by first cutting a continuous cylindrical shaft at an angle of about 15° to about 60°, preferably about 45° with respect an axis of the cylindrical shaft to form a needle blank having a planar angle cut tip. Thereafter, the outer surface 24 of the distal portion of the angle cut needle blank may be beveled to form the beveled surface 26 and to form a cutting edge 28 of the hypodermic needle along the internal surface 22 at the distal end of the needle. The location of the cutting edge 28 at the inner diameter of the hypodermic needle 20 is most clearly illustrated in the end view of FIG. 5. According to this configuration, the leading portion of the cutting edge 28 of the present invention is positioned at the inner diameter or inner surface 22 of the needle, rather than at the prior art position, at the outer diameter or outer surface of the needle.

As shown in FIG. 4, the beveled surface 26 of the hypodermic needle 20 according to the present invention forms a cutting edge 28 at the intersection between the beveled surface 26 and the inner surface 22 of the needle. This cutting edge 28 possesses a substantially continuous oval shape as most clearly shown in FIG. 3. As shown in the cross-sectional view of FIG. 4, the angle α between the beveled edge 26 and the inner surface 22 of the needle shaft at the forward or distal portion of the cutting edge is smaller than the angle β between the beveled edge 26 and the inner surface 22 at the trailing proximal cutting edge. The angle β is about 15° to about 60°, preferably about 45°. The angle α between the beveled edge 26 and the inner surface of the needle shaft is about 15° to about 60°, preferably about 40°.

As shown in FIG. 4, the cutting edge 28 preferably lies entirely within a plane which is at the same angle β as the plane of the beveled edge 26 at the center of the trailing proximal cutting edge. However, the cutting edge 28 may alternatively be formed as a slightly concave or convex edge when viewed from the side of the needle, as in FIG. 4.

The beveling of the exterior edge of the hypodermic needle 20 according to the present invention provides a smaller and sharper point than the point of a conventional needle of the same diameter because the point is formed at the arc of the inner diameter of the needle shaft as opposed to the arc of the exterior diameter which is larger. This smaller and sharper leading cutting edge of the present invention punctures tissue more easily than the conventional needle and causes less tissue trauma than the conventional needle. The smaller area of cutting causes trauma to a smaller area of tissue and thus, less painful stimulation of nerve endings during penetration. Also less post procedure recovery time, and less bruising and inflammation.

The conventional hypodermic needle, such as the needle 10 shown in FIGS. 1 and 2, also causes tissue trauma due to compression of the tissue which has been punctured by the leading cutting edge and is then pushed from the leading cutting edge into the bore of the needle. This tissue trauma is avoided by the hypodermic needle 20 according to the present invention in which, due to the location of the cutting edge 28 at the inner diameter of the needle, there is no jamming, pushing, or compression of tissue from the leading cutting edge into the bore of the needle.

Additional advantages of the location of the cutting edge 28 according to the present invention include the fact that the tissue being cut is more taut due to the configuration of the cutting edge 28 and is easier to penetrate than with conventional hypodermic needles. In addition, the tissue which is not being cut is spread away from the cutting edge 28 and away from the bore by the beveled surface 26. Further, the needle can be more easily threaded through blood vessels, tunnel incisions, or cavities because the tip of the needle is offset from the outer circumference of the needle.

Another important advantage of the present invention is illustrated by FIGS. 10 and 11 in which the conventional hypodermic needle 10 and the hypodermic needle 20 of the present invention are each shown inserted into a blood vessel 50. As discussed above in connection with FIG. 11, the leading cutting edge 14 of the conventional needle 10 is likely to puncture an opposite side wall of the blood vessel 50 if the needle is allowed to penetrate too deeply into the blood vessel. In contrast, the hypodermic needle 20 according to the present invention will be much less likely to penetrate the opposite wall of the blood vessel 50 because the beveled surface 26 prevents the cutting edge 28 from damaging the opposite wall.

The tip of a hypodermic needle 30 according to a second embodiment of the present invention is illustrated in FIGS. 6 and 7. The hypodermic needle 30 includes a substantially cylindrical inner surface 32 and a substantially cylindrical outer surface 34. An exterior beveled surface 36 is formed around the exterior surface of the needle 30 and forms a cutting edge 38 between the beveled surface 36 and the inner surface 32. According to the second embodiment of the invention, the cutting edge 38 includes a sharp leading portion and has a trailing portion 40 which is rounded (i.e., not as sharp as the cutting edge 38) as shown in FIGS. 6 and 7 so that the trailing portion 40 is blunt. The rounded trailing portion 40 is most clearly shown in the detail of FIG. 9, as compared to the detail of FIG. 8 which depicts the embodiment of FIG. 4. The rounded trailing cutting edge 40 allows the tissue to be punctured by the leading cutting edge 38 but prevents a plug of tissue from being cut out by the trailing cutting edge of the needle which can be injected into a patient's tissue or into the blood stream and possibly cause a downstream embolus (blockage of a blood vessel) or an abscess as previously discussed.

The rounded edge 40 of the needle 30 extends around 1% to 60%, preferably to about 50% of the circumference of the needle 30. As the hypodermic needle 30 according to the second embodiment of the invention is inserted, the leading cutting edge 38 makes a curvilinear or an arc shaped cut through the tissue. The needle passes through this curvilinear or arc shaped cut without cutting a plug of tissue. In addition to preventing a plug of tissue, the embodiment of FIGS. 6, 7, and 9 also provides an advantage of faster healing. A curvilinear incision in a blood vessel will seal much more readily than if a tissue plug has been removed.

Figure 13:
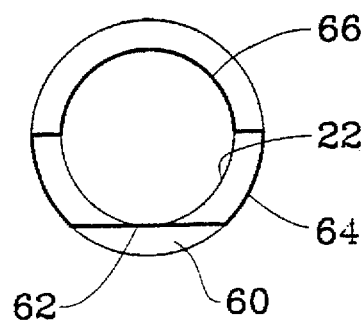
FIG. 13 is an end view of the hypodermic needle of FIG. 12.

The second embodiment of the hypodermic needle 30 provides the same advantages as the first embodiment including prevention of trauma and pain due to the smaller and sharper cutting edge, as well as, the additional advantage of not cutting a plug of tissue. A third embodiment of the present invention is illustrated in FIGS. 12 and 13. According to the third embodiment of the invention, a planar beveled edge 60 forms the leading cutting edge 62 of the needle. The cutting edge of this embodiment includes the leading cutting edge 62 formed from the intersection of the planar beveled edge 60 and the internal surface 22. The cutting edge includes side portions 64 which are formed along the exterior surface 24 of the needle and includes a trailing cutting edge 66 which is formed at the interior surface 22 of the needle. This embodiment provides the advantages associated with a leading cutting edge located at an inner diameter or arc of the needle and a smaller cutting area. In addition, this embodiment is somewhat easier to form because the beveled edge 60 is planar and the formation of this planar bevel may be easier than the formation of a curved surface.

Not only is important to produce a smaller (volume) plug of tissue as with the embodiments of FIGS. 3–5, 8, 12, and 13 because of embolus formation and abscess formation, but even more importantly no plug at all is formed with the embodiment of FIGS. 6, 7, and 9. Another of the dangers of plug formation is that a venous embolus will generally lodge in the lungs and thus is not desirable. However, when an arterial puncture is performed to sample arterial blood an embolus liberated in the arterial system can be organ threatening, limb threatening or even life threatening. Since the arterial system has a high hydrostatic pressure, a single or double perforation can leak leading to exsanguination and even death of the patient. These potentially life threatening complications are all addressed by the various embodiments of the present invention.

While the invention has been described in detail with reference to preferred embodiments thereof, it will be apparent to one skilled in the art that various changes can be made, and equivalents employed without departing from the spirit and scope of the invention.

What is claimed is:

1. A hypodermic needle comprising:
    an internal substantially cylindrical surface, an external substantially cylindrical surface, a distal end formed at an angle with respect to an axis of the needle, a beveled surface extending around a portion of the distal end and forming an acute angle with the internal surface, and an oval leading cutting edge for penetrating skin formed by an intersection of the beveled surface and the internal surface along a distal portion of the internal substantially cylindrical surface.

2. The hypodermic needle according to claim 1, wherein the beveled surface extends around an entire external circumference of the distal end of the needle.

3. The hypodermic needle according to claim 2, wherein the beveled surface forms a first acute angle with the internal surface at the leading distal edge and a second acute angle with the internal surface at the trailing proximal edge.

4. The hypodermic needle according to claim 3, wherein the first acute angle is greater than the second acute angle.

5. The hypodermic needle according to claim 1, wherein the beveled edge has a planar cross-section.

6. The hypodermic needle according to claim 1, wherein the intersection of the beveled surface and the internal surface forms a continuous oval shaped cutting edge.

7. The hypodermic needle according to claim 1, further comprising a rounded intersection between the internal surface and the beveled surface at a trailing portion of the distal end of the needle.

8. The hypodermic needle according to claim 7, wherein the rounded intersection between the internal and beveled surfaces of the needle extends around 1% to 60% of a circumference of the needle.

9. The hypodermic needle according to claim 1, wherein the oval leading cutting edge lies in a single plane.

10. A hypodermic needle comprising:
    a hollow needle shaft having a longitudinal axis and an internal diameter;
    a needle distal end formed at an acute angle with respect to the longitudinal axis of the needle shaft; and
    a leading cutting edge for penetrating skin formed at the internal diameter of the needle shaft and extending in a curved path along at least a portion of an internal circumference of the needle.

11. The hypodermic needle according to claim 10, further comprising a beveled surface formed between the leading cutting edge and an exterior of the needle shaft.

12. The hypodermic needle according to claim 11, wherein the beveled surface forms an obtuse angle with the exterior of the needle shaft.

13. The hypodermic needle according to claim 11, wherein the beveled surface extends around an entire external circumference of the needle shaft.

14. The hypodermic needle according to claim 10, wherein the leading cutting edge is substantially oval.

15. The hypodermic needle according to claim 10, further comprising a blunt trailing cutting edge.

16. The hypodermic needle according to claim 15, wherein the blunt portion of the trailing cutting edge extends around 1% to 60% of the internal circumference of the needle.

17. The hypodermic needle according to claim 10, wherein the leading cutting edge lies in a single plane.

18. The hypodermic needle according to claim 17, wherein the leading cutting edge is oval.

* * * * *